United States Patent [19]

Sawyer et al.

[11] Patent Number: 5,143,710
[45] Date of Patent: Sep. 1, 1992

[54] METHODS FOR PRODUCING SUPEROXIDE ION IN SITU

[75] Inventors: Donald T. Sawyer; Seungwon Jeon; Paul K. S. Tsang, all of College Station, Tex.

[73] Assignee: The Texas A & M University System, College Station, Tex.

[21] Appl. No.: 455,571

[22] Filed: Dec. 22, 1989

[51] Int. Cl.[5] .............................................. C01B 15/04
[52] U.S. Cl. ..................................................... 423/581
[58] Field of Search ......................................... 423/581

[56] References Cited

U.S. PATENT DOCUMENTS 3,260,570  7/1966  Russell .............................. 423/581
4,410,402 10/1983  Sawyer et al. .
4,468,297  8/1984  Sawyer et al. .

OTHER PUBLICATIONS

Thomas S. Calderwood et al., "Oxidation of Substituted Hydrazines by Superoxide Ion: The Initiation Step for the Autoxidation of 1,2-diphenylhydrazine", *J. Am. Chem. Soc.*, (1984), 106, 4683–4687.
Chemical Abstracts 105(25): 221071n.
Sawyer et al.; "Superoxide and Superoxide Dismutase in Chemistry", (1988); pp. 88, 89, 90, and 91.
Roberts et al., Journal of the American Chemical Society, Oxygenation by Superoxide Ion of CCl4, FCCl4, HCCl4, p,p'-DDT and Related Trichloromethyl Substrates (RCCl3) in Aprotic Solvents, 1983.
Sugimoto et al., Journal of the American Chemical Society, Oxygenation of Polychloro Aromatic Hydrocarbons by a Superoxide Ion in Aprotic Media, 1987.
Sugimoto et al., Environmental Science & Technology, Degradation and Dehalogenation of Polychlorobiphenyls and Halogenated Aromatic Molecules by Superoxide Ion and by Electrolytic Reduction, 1988.

Primary Examiner—Wayne Langel
Attorney, Agent, or Firm—Curtis Morris & Safford

[57] ABSTRACT

Three methods are provided for generating superoxide ions in an aprotic solvent. In each method a compound that is dependent on the particular reaction mechanism of the method reacts with dioxygen dissolved in the aprotic solvent and hydroxide ions or alkoxide ions in solution in the aprotic solvent to generate the superoxide ions. In the first method, hydrogen donor compounds such as aniline and N-substituted anilines, or phenylhydrazine and phenylhydrazine derivatives, react with the dioxygen and hydroxide ions or alkoxide ions to generate concentrations of superoxide ions in the aprotic solvent. In the second method, proton donor compounds such as hydroxylamine and N-substituted hydroxylamines react with the dioxygen and hydroxide ions or alkoxide ions to generate concentrations of superoxide ions in the aprotic solvent. In the third method, hydrazine reacts with the dioxygen and hydroxide ions or alkoxide ions to generate superoxide ions in the aprotic solvent when catalyzed by anthraquinone and anthraquinone derivatives. The solution of superoxide ions in an aprotic solvent may then be used to degrade halogenated hydrocarbons.

12 Claims, 1 Drawing Sheet

METHODS FOR PRODUCING SUPEROXIDE ION IN SITU

ACKNOWLEDGMENT

The government has rights in this invention pursuant to Grant No. CHE-8516247 awarded by the National Science Foundation.

BACKGROUND OF THE INVENTION

The invention relates to methods for producing superoxide ions in situ. Specifically, the methods involve the use of a solution of dissolved dioxygen in an aprotic solvent, a compound that provides hydroxide ions in the solution, and a hydrogen donor or proton donor. The hydrogen donor or proton donor reacts with the hydroxide ions and dioxygen in the solution of an aprotic solvent to generate superoxide ions. An anthraquinone catalyst has proven effective to promote the reaction for certain hydrogen donors which otherwise do not react with the hydroxide ions and dioxygen to generate superoxide ions.

Superoxide ions have proven useful in many applications. Superoxide ions are an effective nucleophile in aprotic media. Sugimoto et al. *J. Am. Chem. Soc.* 1988, 110, 5193. Further, biochemists have studied superoxide ions because they are respiratory intermediates. Knowles et al. *Biochem. J.* 1969, 111, 53.

Superoxide ions have proven particularly effective for destroying halogenated hydrocarbons such as polychlorinated biphenyls (PCBs) and similar toxic materials that create environmental hazards. U.S. Pat. Nos. 4,468,297 and 4,410,402, describe the use of superoxide ions for degrading halogenated hydrocarbons and halogenate olefinic hydrocarbons.

The destruction of halogenated hydrocarbons has proven difficult. Many of these compounds react slowly or incompletely with traditional bases; this becomes a significant problem as the number of halogen atoms in the compound increases (U.S. Pat. No. 4,410,402, col. 1, lines 35-41). Superoxide ions overcome this difficulty, and react rapidly with halogenated hydrocarbons when the reaction is carried out in an aprotic solvent. (U.S. Pat. No. 4,410,402, col. 2, lines 34-52).

Several methods have been developed to generate superoxide ions. For example, pulse radiolysis of dioxygen has been used to generate superoxide ions Gebicki et al. *J. Am. Chem. Soc.* 1982, 104, 796. Further, photolysis of hydrogen peroxide in aqueous media, and base-induced decomposition of hydrogen peroxide have also been used to generate superoxide ions. McDowell et al. *Inorg. Chem.* 1983, 22, 847; and Morrison et al. *Inorg. Chem.* 1979, 18, 1971.

Solutions of superoxide ion in aprotic solvents have also been prepared using electrochemical means. Sawyer et al. *Anal. Chem.* 1982, 54, 1720. For example, the superoxide ions used for degrading halogenated hydrocarbons in U.S. Pat. Nos. 4,468,297 and 4,410,402, are generated in a controlled potential electrolysis cell which uses aprotic solvent for the electrolyte. (U.S. Pat. No. 4,410,402, col. 2, lines 53-57; U.S. Pat. No. 4,468,297, col. 2, lines 44-48).

The methods described above for generating superoxide ions suffer from several disadvantages and are not appropriate for all applications. For example, methods for generating superoxide ions based on pulse radiolysis, photolysis, or electrolysis, all require radiation or electrical energy sources. Typically, the energy costs for these methods are prohibitively expensive, especially for applications such as degrading halogenated hydrocarbons on an industrial scale. Likewise, methods for generating superoxide ions based on decomposing hydrogen peroxide may be prohibitively expensive for particular applications due to the cost of hydrogen peroxide. Consequently, other methods for generating superoxide ions are desired.

SUMMARY OF THE INVENTION

The invention comprises three methods for generating superoxide ions in an aprotic solvent. Each method involves a reaction between dioxygen dissolved in the aprotic solvent, hydroxide ions in solution in the aprotic solvent, and a hydrogen donor or proton donor.

In the reaction mechanism of the first method a hydrogen donor reacts with the dioxygen and hydroxide ions to generate superoxide ions. The hydrogen donor comprises aniline or N-substituted aniline compounds such as N-methylaniline or N-phenylaniline, or phenylhydrazine or phenylhydrazine derivatives such as 1,1-diphenylhydrazine or 1-methyl-1-phenylhydrazine.

In the reaction mechanism of the second method a proton donor reacts with the dioxygen and hydroxide ions to form superoxide ions. The proton donor comprises hydroxylamine or N-substituted hydroxylamines such as N-methylhydroxylamine or N,N'-dimethylhydroxylamine.

In the reaction mechanism of the third method a hydrogen donor reacts with the dioxygen and hydroxide ions to generate superoxide ions when catalyzed by anthraquinone or other quinones such as 2-ethylanthraquinone or 2methylanthraquinone. The hydrogen donor for the third method comprises hydrazine or 1,4-cyclohexadiene.

Dimethyl sulfoxide, dimethylformamide, tetramethylenesulfone, and polyethyleneglycol and the monomethyl ether derivative of polyethyleneglycol may be used as the aprotic solvent. Dimethyl sulfoxide is preferred over other aprotic solvents, however, because it deactivates water which reacts with superoxide ions.

These methods generate superoxide ions in situ in an aprotic solvent without the use of radiation or electrical energy sources such as electrolysis. These methods for generating superoxide ions provide a potentially less costly method for disposing of halogenated hydrocarbons in many applications, and overcome the disadvantage of conventional methods of halogenated hydrocarbon disposal that generate superoxide ions by electrolysis The methods of the invention also generate the superoxide ions in an aprotic solvent, which is typically used as the medium for the degradation reaction between superoxide ions and halogenate hydrocarbons. Thus, the solution of aprotic solvent that contains superoxide ions generated by the methods of the invention can be used to dispose of halogenated hydrocarbons by simply adding the halogenated hydrocarbons to the solution. The solution of aprotic solvent containing superoxide ions will then degrade halogenated hydrocarbons as described in U.S. Pat. Nos. 4,468,297 and 4,410,402. Further, the solution of superoxide ions generated by the methods of the invention may be used to decontaminate equipment, such as transformers that contain halogenated hydrocarbons, by rinsing the equipment with the solution of aprotic solvent and superoxide ions.

DETAILED DESCRIPTION OF THE INVENTION

Figure 1:
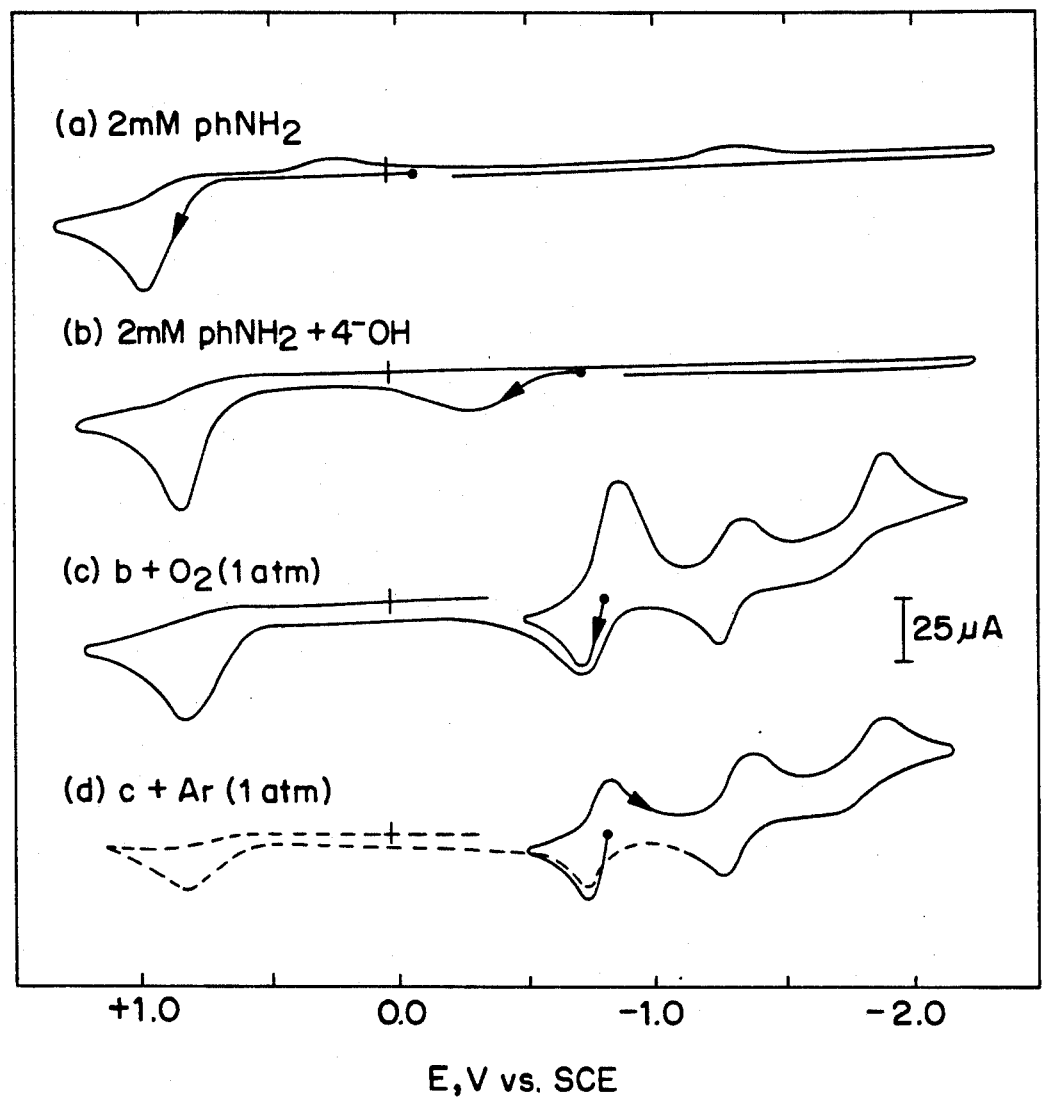
FIG. 1 depicts cyclic voltammograms for (a) aniline (PhNH$_2$); (b) aniline (PhNH$_2$) in the presence of hydroxide ion (OH$^-$); (c) aniline (PhNH$_2$) in the presence of hydroxide ion (OH$^-$) and dioxygen (O$_2$); and (d) the product solution of (c) after deaeration with argon (Ar).

The invention comprises three methods for generating superoxide ions (O$_2^-$·) in situ in an aprotic solvent. More particularly, the superoxide ions are generated in solutions of aprotic solvents that are saturated with dissolved dioxygen (O$_2$) and contain hydroxide ions (OH$^-$), or alkoxide ions (RO$^-$). The first method involves a hydrogen transfer mechanism; the second method involves a proton transfer mechanism; and the third method involves a hydrogen transfer method promoted by a catalyst.

The reactions of the three methods are carried out in a solution of an aprotic solvent. Aprotic solvents are used as the solvent for the methods of the invention because they are conducive to the reactions necessary to generate the superoxide ions. Such solvents are well known; see Sawyer et al., EXPERIMENTAL ELECTROCHEMICAL FOR CHEMISTS, John Wiley & Sons, New York, 1974, pp. 167–215. Aprotic solvents generally have hydrogen bound only to carbon and are at best poor hydrogen-bond donors; they are weakly acidic and proton exchange occurs slowly. The presence of acidic hydrogen in the solution of the methods of the invention interferes with the generation of superoxide ions. Common aprotic solvents include various amides, nitrile, chlorinated hydrocarbons, ethers and other materials; specific examples include acetone, pyridine, nitromethane, nitrobenzene, acetonitrile, benzonitrile, dimethylformamide, N-methyl-2-pyrrolidone, propylene carbonate, dimethyl sulfoxide, sulfolane, and hexamethylphosphoramide. Preferably, aprotic solvents such as dimethyl sulfoxide, dimethylformamide, tetramethylenesulfone, and polyethyleneglycol and its monomethyl ether derivative are used for the methods of the invention.

Many compounds may be used as the source of hydroxide and alkoxide ions in the aprotic solvent. For example, (Bu$_4$N)OH, (Me$_4$N)OH.5H$_2$O, KOH, NaOH, Na(PEG), K(PEG), K(MePEG), Na(MePEG), (Bu$_4$N)PEG, (Me$_4$N)PEG, KOMe, NaOMe, (Me$_4$N)OMe, K$_2$CO$_3$, Na$_2$CO$_3$, CaCO$_3$, KHCO$_3$, NaHCO$_3$, K$_3$PO$_4$, Na$_3$PO$_4$, CaO, NaAlO$_2$, and Na$_2$ZnO$_2$ may be added to the aprotic solvent to provide hydroxide ions or alkoxide ions.

The hydrogen transfer method uses aniline and its derivatives or phenylhydrazine and its derivatives as a hydrogen donor to react with hydroxide ions or alkoxide ions and dioxygen in an aprotic solvent to generate superoxide ions. Example 1 describes experimental data obtained for reactions using the hydrogen transfer method of generating superoxide ions.

The reaction mechanism for the hydrogen transfer method when aniline (PhNH$_2$) is the hydrogen donor appears to be as follows:

2 PhNH$_2$ +2 OH$^-$ +3 O$_2$ →
[PhN(H)OON(H)Ph]+2 O$_2^-$· +2 H$_2$O
[PhN(H)OON(H)Ph] → PhN=NPh + HOOH to give an overall reaction as follows:

2 PhNH$_2$ +2 OH$^-$ +3 O$_2$ → 2 O$_2^-$· +PhN=NPh + HOOH +2 H$_2$O

The hydroxide ion (OH$^-$) acts as a one-electron reducing agent towards the dioxygen (O$_2$), and is facilitated by the available hydrogens of the aniline (PhNH$_2$). The aniline (PhNH$_2$) appears to form radicals which are stabilized by radical coupling to dioxygen (O$_2$) to form the intermediate [PhN(H)OON(H)Ph] which in turn decomposes into azobenzene (PhN=NPh) and hydrogen peroxide (HOOH).

N-substituted anilines such as N-methylaniline (PhNHMe) and N-phenylaniline (PhNHPh) also act as hydrogen donors, like aniline, to give similar yields of superoxide ions when reacted with hydroxide ions and dioxygen in an aprotic solvent. Further, phenylhydrazine (PhNHNH$_2$), 1,1-diphenylhydrazine (Ph$_2$NNH$_2$), and 1-methyl-1-phenylhydrazine [Ph(Me)NNH$_2$] also act as hydrogen donors, like aniline, to give similar yields of superoxide ions when reacted with hydroxide ions and dioxygen in an aprotic solvent. The reaction when phenylhydrazine (PhNHNH$_2$) is the hydrogen donor is as follows:

2 PhNHNH$_2$ +2 OH$^-$ +3 O$_2$ → 2 O$_2^-$· +2 PhH +2 N$_2$+HOOH +2 H$_2$O

Thus, it appears that primary and secondary aromatic amines, and phenylhydrazines may be used as hydrogen donor compounds for this method.

The proton transfer method uses hydroxylamine and its derivatives as a proton donor which reacts with hydroxide ions and dioxygen in an aprotic solvent to generate superoxide ion. Example 2 describes experimental data obtained for reactions using the proton donor method for generating superoxide ions.

The reaction mechanism for the proton donor method when hydroxylamine is the proton donor appears to be as follows:

H$_2$NOH + OH$^-$ → H$_2$NO$^-$ +H$_2$O

2 H$_2$NO$^-$ +2 O$_2$ → 2 h$_2$NO· +2 O$_2^-$·

2 H$_2$NO· → [H$_2$NOONH$_2$]

[H$_2$NOONH$_2$] +2 OH$^-$ +2 O$_2$ → 2 NO$_2^-$ +HOOH +2 H$_2$O to give an overall reaction of:

2 H$_2$NOH +4 OH$^-$ +2 O$_2$ → 2 NO$_2^-$ +HOOH +4 H$_2$O

In the first step of the reaction mechanism the hydroxylamine (H$_2$NOH) is deprotonated by hydroxide ion (OH$^-$) to form the anion (H$_2$NO$^-$) and water (H$_2$O). In the second step the anion (H$_2$NO$^-$) gives up an electron to dioxygen (O$_2$) to form the radical (H$_2$NO·) and superoxide ion (O$_2^-$·). Two of the radicals (H$_2$NO·) are stabilized by coupling to give an intermediate [H$_2$NOONH$_2$], which in turn reacts with hydroxide ion (OH$^-$) and dioxygen (O$_2$) to give nitrite ion (NO$_2^-$), hydrogen peroxide (HOOH), and water (H$_2$O).

It appears that the oxygen atom of the hydroxylamine is involved in attack on the dioxygen because O-methylhydroxylamine and O-benzylhydroxylamine have proven unreactive in this context. In contrast, N-methylhydroxylamine and N,N-dimethylhydroxylamine are rapidly oxidized in alkaline aprotic solutions.

The catalytic hydrogen transfer method uses anthraquinone (AQ) or its derivatives to promote a reaction between a hydrogen donor, hydroxide ions, and dioxygen in an aprotic solvent to generate superoxide ions. Example 3 describes experimental data obtained for reactions using the catalytic hydrogen transfer method for generating superoxide ions.

Without the anthraquinone the hydrazine does not react with the hydroxide ions or the dioxygen. The reaction mechanism for this method appears to be:

$$AQ + OH^- \rightleftharpoons [AQ(OH)^-]$$

$$[AQ(OH)^-] + \tfrac{1}{2}H_2NNH_2 \rightarrow AQ^{-\cdot} + H_2O + \tfrac{1}{4}N_2$$

$$AQ^{-\cdot} + O_2 \rightleftharpoons AQ + O_2^{-\cdot}$$

No anthraquinone (AQ) is consumed in the reaction mechanism. Thus the overall reaction is:

$$H_2NNH_2 + 4 O_2 + 4 OH^- \rightarrow 4 O_2^{-\cdot} + N_2 + 4 H_2O$$

Dioxygen is not added to the solution until the first step of the reaction has reached equilibrium.

Other quinones effective for catalyzing the reaction between hydrazine, hydroxide ions, and dioxygen are 2-ethylanthraquinone (2-EtAQ), 2-methylanthraquinone (2-MeAQ), 1,4-naphthoquinone (NQ), and 1,4-benzoquionone (Q). The relative reaction rates for the quinones are in the order 2- EtAQ~2-MeAQ->AQ>NQ>Q. Similar catalytic effects are also obtained for hydrated quinones.

Anthraquinone has also been used to catalyze a reaction between 1,4-cyclohexadiene (1,4-CHD), as a hydrogen donor instead of hydrazine, with hydroxide ions and dioxygen to produce superoxide ions. The overall reaction for this is:

$$O_2 + 2 OH^- + 1,4\text{-CHD} \rightarrow 2 O_2^{-\cdot} + 2 H_2O + PhH$$

Dimethyl sulfoxide is preferred over dimethylformamide and acetonitrile as the aprotic solvent because only low concentrations of superoxide ions are present in these solvents when the reaction is carried out. It appears that the water produced by the reaction disproportionates the superoxide ion and reduces the yield of superoxide ion when dimethylformamide and actonitrile are the aprotic solution. Dimethyl sulfoxide, on the other hand, deactivates water and tends to avoid this effect.

Generally the methods of the invention are carried out by adding the compound that provides the source of hydroxide ions to the selected aprotic solvent and then adding the selected hydrogen donor or proton donor. Next, anthraquinone or its derivative is added if a catalyst is necessary to promote the reaction for the hydrogen donor that is selected. Dioxygen is then dissolved in the solution by bubbling dioxygen gas through the solution. The reaction generating the superoxide ions proceeds as the dioxygen is being bubbled through the solution.

EXAMPLE 1

A solution of aniline (PhNH$_2$) in dimethyl sulfoxide which was saturated with dioxygen (O$_2$) was prepared. The solution included concentrations of 5.5 mM (millimolar) of aniline and 2.1 mM of dioxygen (at 1 atmosphere). The dimethyl sulfoxide used was "distilled in glass" grade without further purification. The aniline used was "99.5+per pure" and was used without further purification.

Excess hydroxide ion (OH$^-$) in the form of tetrabutylammonium hydroxide [(Bu$_4$N)OH] was added to the solution to achieve a concentration of 22 mM of OH$^-$ions. The tetrabutylammonium hydroxide and other reagents used in the experiments of the examples were analytical grade or the highest available grade and were used without further purification.

The excess hydroxide ions (OH$^-$), dissolved dioxygen (O$_2$), and aniline (PhNH$_2$) reacted in the dimethyl sulfoxide solution to form superoxide ions (O$_2^{-\cdot}$), azobenzene (PhN=NPh), hydrogen peroxide (HOOH), and water (H$_2$O). The dioxygen was introduced by bubbling gaseous dioxygen through the solution of other reactants for 20 minutes, and then purging with argon. The reaction yielded concentrations of 1.4 mM of superoxide ions and 2.5 mM of azobenzene.

Table 1 indicates the yields of superoxide ions (O$_2^{-\cdot}$) and azobenzene (PhN=NPh) in both mM concentration and % yield of the stoichiometrically expected amount according to the reaction for the hydrogen transfer method when aniline is the hydrogen donor for various starting concentrations of aniline (PhNH$_2$) and various amounts of excess hydroxide ions (OH$^-$).

TABLE 1

| Yields of O$_2^{-\cdot}$ and PhN=NPh, mM (%) | | |
|---|---|---|
| PhNH$_2$ mM | O$_2^{-\cdot}$ mM (%) | PhN=NPh mM (%) |
| 1:1 OH$^-$:PhNH$_2$ mol-ratio (unreacted PhNH$_2$ present): | | |
| 1.1 | 0.3 (30) | 0.2 (33) |
| 2.2 | 0.4 (19) | 0.4 (35) |
| 5.5 | 0.7 (13) | 0.9 (34) |
| 11.0 | 1.3 (12) | 2.4 (43) |
| 2:1 OH$^-$:PhNH$_2$ mol-ratio (unreacted PhNH$_2$ present): | | |
| 1.1 | 0.4 (40) | 0.3 (56) |
| 2.2 | 0.6 (26) | 0.7 (63) |
| 5.5 | 1.1 (20) | 1.6 (59) |
| 11.0 | 1.5 (14) | 3.3 (60) |
| 4:1 OH$^-$:PhNH$_2$ mol-ratio: | | |
| 1.1 | 0.6 (51) | 0.5 (87) |
| 2.2 | 1.0 (47) | 0.9 (84) |
| 5.5 | 1.4 (26) | 2.5 (89) |
| 11.0 | 2.4 (22) | 4.9 (89) |
| 10:1 OH$^-$:PhNH$_2$ mol-ratio: | | |
| 1.1 | 1.1 (97) | 0.5 (93) |
| 2.2 | 1.9 (84) | 1.0 (91) |
| 5.5 | 2.0 (36) | 2.6 (93) |
| 11.0 | 1.6 (15) | 5.0 (91) |

The yields of superoxide ions and azobenzene were determined by linear sweep voltammetry. The azobenzene concentration was also determined by UV absorption spectroscopy.

FIG. 1 depicts cyclic voltammograms for: (a) aniline dissolved in dimethyl sulfoxide at a concentration of 2 mM; (b) the solution of (a) to which hydroxide ions have been added to achieve a hydroxide ion to aniline mol-ratio of 2:1; (c) the solution of (b) with dioxygen dissolved in the solution at one atmosphere; and (d) the product solution of (c) after purging the solution with argon. The depth of the minimum for the curve at −0.7 V in voltammograms (c) and (d) indicates the concentration of superoxide ion that has been generated in situ.

Ideally, according to the stoichiometry of the overall equation for the reaction of aniline with hydroxide ions and dioxygen the moles of superoxide ions generated should be equal to the moles of aniline consumed. The percent yields of superoxide ions (O$_2^{-\cdot}$) in Table 1 indicate that this is not the case. It is believed that residual water causes the superoxide ions to disproportionate according to the following reaction:

$2 O_2^-. + H_2O \rightarrow O_2 + HOO^- + OH^-$

Nevertheless, Table 1 indicates that if a large excess of $OH^-$ is used the amount of superoxide ion produced is very near the stoichiometric amount.

Likewise, Table 2 indicates the yields of superoxide ions for the N-substituted anilines: N-methylaniline (PhNHMe), and N-phenylaniline (PhHNPh); and phenylhydrazines: phenylhydrazine (PHNHNH$_2$), 1,1-diphenylhydrazine (Ph$_2$NNH$_2$), and 1-methyl-1-phenylhydrazine [Ph(Me)NNH$_2$].

TABLE 2

Yields of $O_2^-$., mM (%)

| | OH$^-$:PhNHMe mol-ratio | | |
|---|---|---|---|
| PhNHMe (mM) | 2:1 | 4:1 | 10:1 |
| 1.8 | 0.6 (30) | 0.8 (45) | 1.4 (77) |
| 4.6 | 1.2 (26) | 2.2 (48) | 3.4 (73) |
| 9.2 | 2.6 (28) | 4.8 (52) | 4.5 (49) |

| | OH$^-$:PhNHPh mol-ratio | | |
|---|---|---|---|
| PhNHPh (mM) | 2:1 | 4:1 | 10:1 |
| 2.0 | — | 1.2 (60) | 1.8 (90) |
| 3.6 | 1.0 (26) | — | — |
| 4.6 | — | 2.7 (58) | 4.0 (88) |
| 10.0 | 1.6 (16) | 5.6 (56) | 6.9 (69) |
| 12.4 | — | 5.9 (48) | — |

| | OH$^-$:PhNHNH$_2$ mol-ratio | | |
|---|---|---|---|
| PhNHNH$_2$ (mM) | 2:1 | 4:1 | 10:1 |
| 3.5 | — | 0.9 (45) | 1.0 (50) |
| 5.5 | — | 1.4 (28) | 1.8 (36) |
| 10.0 | — | 1.8 (18) | 2.6 (26) |

| | OH$^-$:Ph$_2$NNH$_2$ mol-ratio | | |
|---|---|---|---|
| Ph$_2$NNH$_2$ (mM) | 2:1 | 4:1 | 10:1 |
| 3.5 | — | 0.6 (17) | 1.4 (40) |
| 5.1 | — | 1.0 (20) | 1.5 (29) |

| | OH$^-$:Ph(Me)NNH$_2$ mol-ratio | | |
|---|---|---|---|
| Ph(Me)NNH$_2$ (mM) | 2:1 | 4:1 | 10:1 |
| 4.2 | — | 1.0 (24) | 1.3 (31) |

EXAMPLE 2

Experiments were conducted to determine the ability of hydroxylamine and its derivatives to generate superoxide ions when reacted with dioxygen and hydroxide ions in an aprotic solvent. Table 3 indicates the yields of superoxide ions ($O_2^-$.) for various concentrations of hydroxylamine and its derivatives.

TABLE 3

Yield $O_2^-$., mM (%)

*In dimethyl sulfoxide solvent:*

| | OH$^-$:H$_2$NOH | |
|---|---|---|
| H$_2$NOH mM | 4:1 | 10:1 |
| 1.4 | 0.7 (50) | 0.9 (64) |
| 4.3 | 1.7 (37) | 2.0 (46) |
| 5.4 | 1.6 (30) | 2.0 (37) |

| | OH$^-$:MeNHOH | |
|---|---|---|
| MeNHOH mM | 4:1 | 10:1 |
| 4.3 | 1.3 (30) | 1.5 (35) |

| | OH$^-$:Me$_2$NOH | |
|---|---|---|
| Me$_2$NOH mM | 4:1 | 10:1 |
| 1.8 | 1.0 (55) | 1.4 (77) |
| 3.8 | 1.3 (34) | 1.4 (37) |

TABLE 3-continued

Yield $O_2^-$., mM (%)

| | | |
|---|---|---|
| 6.5 | 1.5 (23) | 1.7 (26) |

*In dimethylformamide solvent:*

| | OH$^-$:H$_2$NOH | |
|---|---|---|
| H$_2$NOH mM | 4:1 | 10:1 |
| 4.6 | 2.4 (52) | 3.1 (67) |
| 12.4 | 2.4 (52) | 4.3 (35) |

The apparent yield of superoxide ions is low when hydroxylamine (H$_2$NOH) was used as proton donor because the superoxide ion ($O_2^-$.) reacts with hydroxylamine (H$_2$NOH) to produce nitrous oxide (NO) according to the following reaction:

$H_2NOH + 3 O_2^-. \rightarrow NO + 3 HOO^-$

EXAMPLE 3

Experiments were conducted to determine the ability of hydrazine to generate superoxide ions when reacted with dioxygen and hydroxide ions in an aprotic solvent in the presence of anthraquinone or its derivatives. Table 4 indicates the yields of superoxide ions ($O_2^-$.) for the reaction between hydrazine (H$_2$NNH$_2$), hydroxide ions (OH$^-$), and dioxygen (O$_2$) in the presence of anthraquinone (AQ), 2-ethylanthraquinone (2EtAQ), 2-methylanthraquinone (2-MeAQ), 1,4-maphthoquinone (NQ), and 1,4-benzoquionone (Q).

TABLE 4

Yields of $O_2^-$., mM (%)

| AQ mM | H$_2$NNH$_2$ mM | OH$^-$ mM | $O_2^-$. mM (%) |
|---|---|---|---|
| 0.5 | 3.0 | 12.0 | 3.8 (32) |
| 0.5 | 6.0 | 24.0 | 6.4 (27) |
| 0.5 | 9.0 | 36.0 | 8.2 (23) |
| 1.0 | 3.0 | 12.0 | 3.5 (29) |
| 1.0 | 6.0 | 24.0 | 6.2 (26) |
| 1.0 | 9.0 | 36.0 | 7.6 (21) |
| 2.0 | 3.0 | 12.0 | 3.1 (26) |
| 2.0 | 9.0 | 36.0 | 6.8 (19) |

| 2-EtAQ mM | H$_2$NNH$_2$ mM | OH$^-$ mM | $O_2^-$. mM (%) |
|---|---|---|---|
| 1.0 | 3.0 | 12.0 | 3.6 (30) |
| 1.0 | 6.0 | 24.0 | 6.3 (26) |
| 1.0 | 9.0 | 36.0 | 8.5 (24) |
| 2.0 | 3.0 | 12.0 | 3.4 (28) |
| 2.0 | 6.0 | 24.0 | 6.1 (25) |
| 2.0 | 9.0 | 36.0 | 8.2 (23) |

| 2-MeAQ mM | H$_2$NNH$_2$ mM | OH$^-$ mM | $O_2^-$. mM (%) |
|---|---|---|---|
| 1.0 | 3.0 | 12.0 | 3.4 (28) |
| 1.0 | 6.0 | 24.0 | 6.2 (26) |
| 1.0 | 9.0 | 36.0 | 8.2 (23) |

| NQ mM | H$_2$NNH$_2$ mM | OH$^-$ mM | $O_2^-$. mM (%) |
|---|---|---|---|
| 1.0 | 3.0 | 12.0 | 3.3 (28) |
| 1.0 | 6.0 | 24.0 | 4.9 (20) |

| Q mM | H$_2$NNH$_2$ mM | OH$^-$ mM | $O_2^-$. mM (%) |
|---|---|---|---|
| 1.0 | 3.0 | 12.0 | 3.3 (28) |
| 1.0 | 6.0 | 24.0 | 3.6 (15) |

The examples and embodiments described above are illustrative of the invention. Changes and modifications can be made without departing from the scope of the invention. It is intended that such changes and modifications fall within the scope of the invention as defined by the appended claims. For example, aprotic solvents other than those used in the experiments described above may be used in practicing the invention. Likewise, other hydrogen donor compounds and proton donor compounds which are recognized by those skilled in the art could be substituted for the hydrogen donor compounds and proton donor compounds described in the examples.

What is claimed is:

1. A method for generating superoxide ion comprising:
   a) preparing a solution of a hydrogen donor in an aprotic solvent;
   b) adding an effective amount of a compound into the solution which produces hydroxide ions in the solution;
   c) adding anthraquinone to the solution; and
   d) dissolving dioxygen int he solution and reacting the hydrogen donor, the dissolved dioxygen and the hydroxide ions or alkoxide ions as reactants to produce a concentration of superoxide ions in the solution.

2. The method of claim 1 wherein the anthraquinone is replaced by 2-ethylanthraquinone, 2-methylanthraquinone, 1,4-napthoquinone, or 1,4-benzoquinone.

3. The method of claim 1 wherein the hydrogen donor is hydrazine.

4. The method of claim 1 wherein the hydrogen donor is 1,4-cyclohexadiene.

5. The method of claim 1 wherein the aprotic solvent is dimethyl sulfoxide, dimethyl-formamide, acetonitrile, tetramethylenesulfone, polyethyleneglycol a monomethyl ether of polyethyleneglycol, or a dimethyl ether of polyethyleneglycol.

6. The method of claim 1 wherein the aprotic solvent is dimethyl sulfoxide.

7. The method of claim 1 wherein the compound which produces a concentration of hydroxide ions is a hydroxide compound.

8. The method of claim 1 wherein the compound which produces a concentration of alkoxide ions is an alkoxide compound.

9. The method of claim 1 wherein the compound which produces a concentration of hydroxide ions or alkoxide ions is $(Bu_4N)OH$, $(Me_4N)OH \cdot 5H_2O$, KOH, NaOH, Na(PEG), K(PEG), K(MePEG), Na(MePEG), $(Bu_4N)PEG$, $(Me_4N)PEG$, KOMe, NaOMe, $(Me_4N)OMe$, $K_2CO_3$, $Na_2CO_3$, $CaCO_3$, $KHCO_3$, $NaHCO_3$, $K_3PO_4$, $Na_3PO_4$, CaO, $NaAlO_2$, or $Na_2ZnO_2$.

10. A method for generating superoxide ion comprising:
    a) preparing a solution of a first compound taken from the group consisting of hydrazine and 1,4-cyclohexadiene in an aprotic solvent;
    b) adding an effective amount of a second compound into the solution which produces hydroxide ions in the solution;
    c) adding a third compound taken from the group consisting of anthraquinone, 2-ethylanthraquinone, 2-methylanthraquinone, 1,4-napthoquinone, of 1,4-benzoquinone to the solution; and
    d) dissolving dioxygen in the solution and reacting the first compound, the dissolved dioxygen and the hydroxide ions or alkoxide ions as reactants to produce a concentration of superoxide ions in the solution.

11. The method of claim 10 wherein the aprotic solvent is demethyl sulfoxide.

12. The method of claim 10 wherein the compound which produces alkoxide ions in the solution is an alkoxide.

* * * * *